United States Patent [19]

Blaber et al.

[11] Patent Number: 5,219,569
[45] Date of Patent: Jun. 15, 1993

[54] PROTEASE RESISTANT UROKINASE

[75] Inventors: Michael Blaber, Brisbane; Herbert L. Heyneker, Hillsborough; Gordon A. Vehar, San Carlos, all of Calif.

[73] Assignee: Genentech, Inc., South San Francisco, Calif.

[21] Appl. No.: 766,858

[22] Filed: Aug. 16, 1985

Related U.S. Application Data

[63] Continuation-in-part of Ser. No. 725,468, Apr. 22, 1985, abandoned.

[51] Int. Cl.$^5$ .............................. A61K 37/547; C12N 9/72
[52] U.S. Cl. .............................. 424/94.63; 424/94.64; 435/211; 435/212; 435/215; 435/226
[58] Field of Search .................. 435/215, 212, 211; 424/94.64, 94.63

[56] References Cited

U.S. PATENT DOCUMENTS 4,381,346  4/1983  Huasin et al. .......................... 435/215

FOREIGN PATENT DOCUMENTS 0037687  10/1981  European Pat. Off. ......... 435/172.3
0092182  10/1983  European Pat. Off. .
 210279   2/1987  European Pat. Off. .
0236040   9/1987  European Pat. Off. .
8604351   7/1986  Japan .

OTHER PUBLICATIONS

Tate, K. et al., *Biochemistry*, vol. 26, pp. 338-343, 1987.
Nelles, L. et al., *Chem. Abst.* 106:208738m, p. 177, 1987.
Holmes, W. et al., *Bio/Technology*, vol. 3, pp. 923-929, Oct., 1985.
Winkler, M. et al., *Bio/Technology*, vol. 3, pp. 990-1000, Nov., 1985.
Nelles, L. et al., *J. Biolog. Chem.*, vol. 262, pp. 5682-5689, Apr., 1987.
Pennica, D. et al., *Nature*, vol. 301, pp. 214-221, 1983.

*Primary Examiner*—Richard A. Schwartz
*Assistant Examiner*—Nancy Vogel
*Attorney, Agent, or Firm*—Walter H. Dreger

[57] ABSTRACT

Novel single-chain protease resistant urokinase derivatives are provided. In particular, derivatives are provided wherein the $Lys_{135}Lys_{136}$ and $Arg_{156}$ to $Lys_{158}$ sites are rendered less susceptible to proteolytic cleavage are provided by occluding the sites or by covalently modifying them. Preferred covalent modifications are amino acid sequence variants at the sites where proteolysis of urokinase occurs. These are optimally produced by synthesis of single-chain urokinase mutants in recombinant cell culture. The novel urokinase derivatives herein offer the advantage of avoiding the generation of substantial two-chain urokinase, either in vivo or during recombinant cell culture. However, the derivatives continue function to activate plasminogen in initiating blood clot lysis.

11 Claims, 4 Drawing Sheets

Fig. 1A.

```
GTCCCCGCAGGCCGTCGGCCCCTCCTGCCGCAGGCCACCGAGCCGCCGCCGTCTAGCGCCCGACCTGCCACC
                                              -10                    50
    met arg ala leu leu ala arg leu leu cys val leu val ser asp ser lys gly
-20 ATG AGA GCC CTG CTG GCG CGC CTG CTC TGC GTC CTG GTC AGC GAC TCC AAA GGC
                                                                            20
  1                                             10
    ser asn glu leu his gln val pro ser asn cys asp cys leu asn gly gly thr cys val
    AGC AAT GAA CTT CAT CAA GTT CCA TCG AAC TGT GAC TGT CTA AAT GGA GGA ACA TGT GTG
                            150                 30                              40
    ser asn lys tyr phe ser asn ile his trp cys tyr glu gly tyr arg lys phe gly gly gln
    TCC AAC AAG TAC TTC TCC AAC ATT CAC TGG TGC TAC GAG GGG TAT CGA AAA TTC GGA GGG CAG
        200                         50                             250              60
    his cys glu ile asp lys ser lys thr cys tyr cys pro lys pro asn gly gly his phe tyr arg gly
    CAC TGT GAA ATA GAT AAG TCA AAA ACC TGT TAT TGC CCA AAG AAT GGT CAC TTT TAC CGA GGA
                                    70                  300                         80
    lys ala ser thr asp thr met gly arg his ala leu gln leu pro trp asn ser ala thr val leu
    AAG GCC AGC ACT GAC ACC ATG GGC CAC GCC CAG CTG CCC TGG AAC TCT GCC ACT GTC CTT
                            400                 90                              100
    gln thr tyr arg asn pro asp ala his arg ser arg arg ala leu gln leu pro trp asp thr tyr arg asn asp ala leu gln leu gly lys his asn
    CAG ACG TAC AGA GAC GCC GAT GCT CTT CAG CTG GGC AAA CAT AAT
                                                                120
    tyr cys arg asn pro asp ala arg arg pro trp cys tyr val gln val gly leu lys
    TAC TGC AGG AAC CGG AGG CCC TGG TGT TAT GTG CAG GTG GGC CTA AAG
    450                                 110                         140
    pro leu val gln glu cys met val his asp cys ala asp gly lys lys pro ser ser pro
    CCG CTT GTC CAA GAG TGC ATG GTG CAT GAC TGC GCA GAT GGA AAA AAG CCC TCT CCT
    500                                 130                         550
```

Fig. 1B.

```
pro glu leu lys phe gln cys gly gln lys thr leu arg pro arg phe lys ile ile
CCA GAA TTA AAA TTT CAG TGT GGC CAA AAG ACT CTG AGG CCC CGC TTT AAG ATT ATT
                            150                         600         160 gly glu phe thr thr ile gln pro trp phe ala arg pro ala ile tyr arg arg his
GGA GAA TTC ACC ACC ATC CAG CCC TGG TTT GCG AGG CCC GCC ATC TAC AGG AGG CAC
                            170     650                         180 arg gly ser val thr tyr val cys gly ser leu ile ser pro cys trp val ile
CGG GGC TCT GTC ACC TAC GTG TGT GGA AGC CTC ATC AGC CCT TGC GTG GTG ATC
                            190     700                         200 ser ala thr his cys phe ile asp tyr lys glu asp tyr ile val tyr leu gly
AGC GCC ACA CAC TGC TTC ATT GAT TAC AAG GAG GAC TAC ATC GTC TAC CTG GGT
                            210     750                         220 arg ser arg leu asn ser asn thr gln gly met lys phe glu val glu asn leu ile
CGC TCA AGG CTT AAC TCC AAC ACG CAA GGG ATG AAG TTT GAG GTG GAA AAC CTC ATC
    800                     230                         850         240 leu his lys asp tyr ser ala asp thr leu his his asn asp ile ala leu leu lys
CTA CAC AAG GAC TAC AGC GCT GAC ACG CTT CAC CAC AAC GAC ATT GCC TTG CTG AAG
                            250                     900             260 ile arg ser lys glu gly gly arg cys ala gln pro ser arg thr ile gln thr ile cys leu
ATC CGT TCC AAG GAG GGC AGG TGT GCG CAG CCA TCC CGG ACT ATA CAG ACC TGC CTG
                            270     950                         280
```

Fig.1C.

```
                                        290 gly  thr  ser  cys  glu  ile  thr  gly  phe  gly  300
pro  ser  met  tyr  asn  asp  pro  gln  phe      GGC  ACA  AGC  TGT  GAG  ATC  ACT  GGC  TTT  GGA  lys
CCC  TCG  ATG  TAT  AAC  GAT  CCC  CAG  TTT                                                        AAA
                                        1000
                                                                                                   320
glu  asn  ser  thr  asp  pro  leu  tyr  pro  tyr  leu  gln  leu  lys  met  thr  val  val  lys  leu ile
GAG  AAT  TCT  ACC  GAC  CCC  CTC  TAT  CCG  TAT  CTC  GAG  CTG  AAA  ATG  ACT  GTT  GTG  AAG  CTG ATT
                    1050
                                        330 tyr  gly  val  thr  thr  lys  met          340
ser  his  arg  glu  cys  gln  pro  his      TAC  GGC  GTC  ACC  ACC  AAA  ATG  leu
TCC  CAC  CGG  GAG  TGT  CAG  CCC  CAC  tyr                                    CTA
     1100                                   TAC                                1150
                                        350                                            360
cys  ala  ala  asp  pro  gln  trp  lys  thr  ser  cys  gln  gly  asp  ser  gly  gly  pro  leu
TGT  GCT  GCT  GAC  CCC  CAA  TGG  AAA  ACA  TCC  TGC  CAG  GGA  GAC  TCA  GGG  GGA  CCC  CTC
                                                                  1200
                                        370                                            380
val  cys  ser  leu  gln  gly  arg  met  thr  asp  ser  gln  gly  ile  val  ser  trp  gly  arg  gly  cys
GTC  TGT  TCC  CTC  CAA  GGC  CGC  ATG  ACT  GAT  TCC  CAG  GGA  ATT  GTG  AGC  TGG  GGC  CGT  GGA  TGT
                                                        1250
                                        390                                            400
ala  leu  lys  asp  lys  pro  gly  val  tyr  thr  arg  val  ser  his  phe  leu  pro  trp  ile  arg
GCC  CTG  AAG  GAC  AAG  CCA  GGC  GTC  TAC  ACG  AGA  GTC  TCA  CAC  TTC  TTA  CCC  TGG  ATC  CGC
                                        1300
```

Fig. 1D.

```
                                    410 411
ser his thr lys glu glu asn gly leu ala leu OP
AGT CAC ACC AAG GAG GAA AAT GGC CTG GCC CTC TGA  GGGTCCCCAGGGGAGGAAACGGGCACCACCC
                             1350                                                    1400
GCTTTCTGCTGGTGTCATTTTGCAGTAGAGTCATCTCCATCAGCTGTAAGAAGAGACTGGGAAGATAGGCTCTGC
                                    1450
ACAGATGGATTTGCCTGTGGCACCACCAGGGTGAACGACAATAGCTTTACCCTCACGGATAGGCCTGGGTGCTGGCTG
                  1500                                                   1550
CCCAGACCCCTCTGGCCAGGATGGAGGGGTGGTCCTGACTGTCAACATGTTACTGACCAGCAACTTGTCTTTTTCTGGACT
GAAGCCCTGCAGGAGTTAAAAAGGGCAGGGCATCTCCTGTGCATGGGCTCGAAGGGAGAGCCAGCTCCCCGACCGGTG
                      1650                                          1700
GGCATTTGTGAGGCCCATGGTTGAGAAATGAATAATTCCCAATTAGGAAGTGTAAGCAGCTGAGGTCTCTTGAGGGA
                                    1750
GCTTAGCCAATGTGGGAGCAGCGGTTTGGGGAGCAGAGACACTAACGACTTCAGGGCGTGTGAGTGTAAGTGTGAGTAAGAAGCT
                  1800                                          1850
TGTATCAGGAGAAATATATATGTGTGTTTGCACACTTGTGTGTGACTGTGATGCCACACAGAGTGGTCTCTTTCTGGAGAG
                                             1900                                2000
GGTGTCTGATTGTTAAGTCTAAATATTTCCTTAAACTGTGTGACTGTGATGCCACACAGAGTGGTCTCTTTCTGGAGAG
     1950
GTTATAGGTCACTCCTGGGCCCTCTTGGGTCCCCCACGTGACAGTGCCTGGGAATGTACTTATTCGCAGCATGACCT
                                                                            2100
GTGACCAGCACTGTCTCAGTTTCACTTTCACATAGATGTCCCTTTCTTGGCCAGTTATCCCTTCCTTTTAGCCTAGTT
                                              2150
CATCCAATCCCTCACTGGGTGGGGTGAGGACCACTCCTTACACTGAATATTTATATTTCACTATTTTATATTTATATTTT
                       2200                                             2250
TGTAATTTTAAATAAAGTGATCAATAAATGTGATTTTCTGA
                              2300
```

PROTEASE RESISTANT UROKINASE

This is a continuation-in-part of U.S. Ser. No. 06/725,468, filed Apr. 22, 1985, now abandoned.

BACKGROUND

Urokinase (E.C. 3.4.21.31) is a serine protease which activates plasminogen to plasmin. The protein is synthesized in a variety of tissues including endothelium and kidney, and is excreted in trace amounts into urine. Purified urokinase exists in two active forms, a high molecular weight form (HUK; approximately 50 K) and a low molecular weight form (LUK; approximately 30 K). The entire amino acid sequence of both human forms has been determined (1,2,3). LUK has been shown to be derived from HUK by a proteolytic clip after lysine 135; this clip releases the first 135 amino acids from HUK (1). Conventional wisdom has held that HUK or LUK must be converted to proteolytically active forms by the proteolytic hydrolysis of a single chain precursor, also termed prourokinase, between lysine 158 and isoleucine 159 to generate a two-chain activated form (which continues to correspond to either HUK or LUK). The proteolytically active urokinase species resulting from this hydrolytic clip contain two amino acid chains held together by a single disulfide bond. The two chains formed by the activation clip are termed the A or $A_1$ chains (HUK or LUK, respectively), and the B chain containing the protease domain of the molecule.

Urokinase has been shown to be an effective thrombolytic agent. However, since it is produced naturally in trace quantities the cost of the enzyme is high for an effective dosage. Urokinase has been produced in recombinant cell culture, and DNA encoding urokinase is known together with suitable vectors and host microorganisms (3,8).

As noted above, it has been believed that plasminogen activators exist as proteolytically inactive zymogens that must be "activated" by proteolysis before the enzyme can act upon plasminogen to commence the fibrinolytic cascade (4,5). While it has been observed that the urokinase single-chain proenzyme demonstrates high levels of activity on zymographic and fibrinolytic procedures (4,6), the fact that the proenzyme also exerts only low amidolytic activity on low molecular weight synthetic polypeptide substrates has led to the conclusion that traces of contaminating active (two-chain) urokinase in the proenzyme preparations, or traces of plasmin in the plasminogen used in the fibrin plate assays, accounted for the fibrinolytic activity of prourokinase (4). This in turn would compel the conclusion that single-chain urokinase must be converted to the two-chain form in order to cleave plasminogen and initiate fibrinolysis in vivo.

The role of urokinase in clot lysis in vivo is complicated. Prourokinase now is believed to interact with an inhibitor in plasma. Fibrin is postulated to release this inhibitor, whereupon prourokinase is released for action on plasminogen (7). It is unclear whether removal of the inhibitor alone is sufficient to initiate plasminogen hydrolysis, or whether release from the inhibitor simply facilitates conventional urokinase activation to the two-chain form The urokinase domain bound by the inhibitor is unknown, nor is the binding mechanism known. A further complicating hypothesis attributes a fibrin-binding capability of urokinase to the HUK species, in particular to a region called a "kringle" located within about residues 49 to 132 (8). The relationship of this hypothesis to the inhibitor postulate, and their comparative merit, remains unresolved.

A major impediment to the use of two-chain urokinase for the treatment of blood clots is that the two-chain form is apparently not bound by the putative inhibitor of prourokinase. If two-chain urokinase is administered peripherally it is therefore capable of activating plasminogen at any point within the circulatory system, thereby leading to undesirable side effects. Two-chain urokinase generated by plasmin hydrolysis of single-chain urokinase at the clot site enters circulation with the same adverse side effects, in particular systemic fibrinogenolysis and depletion of $\alpha 2$ anti-plasmin. These side effects hamper proper thrombogenesis in vivo. An improved fora of single-chain urokinase is needed (a) which is capable of binding either fibrin or the postulated inhibitor, i.e., which in the end functions substantially the same as native prourokinase with respect to plasminogen activation at clot sites; (b) which is resistant to proteolytic digestion in particular to conversion to the two-chain form; and (c) which exhibits minimal or no antigenicity in patients to whom it is administered.

SUMMARY

These and other objectives apparent to the skilled artisan are provided by a composition comprising protease resistant single-chain urokinase. Protease resistant single-chain urokinase is produced by combining urokinase with an agent to complex with urokinase or by covalently modifying single-chain urokinase at sites of proteolysis so that the urokinase is no longer susceptible to protease hydrolysis at those locations. The target sites include $Arg_{156}$ to $Lys_{158}$ and, preferably, the site at residues $Lys_{135}$ to $Lys_{136}$. Covalent modifications are accomplished by reacting native urokinase with derivatizing reagents or by the recombinant synthesis of mutants having site specific substitutions, insertions or deletions of amino acid residues at the target site(s). Complexing agents such as antibodies bind to urokinase at the target sites or at flanking sites so that access to the sites by proteases is impeded or prevented. All of these urokinase compositions are designed to reduce or eliminate the proclivity of proteases to cleave at target sites. The conversion of single-chain urokinase to two-chain urokinase by plasmin, bacterial proteases, trypsin and other proteases is impeded by such site specific mutations, thereby reducing undesirable side reactions in vivo, without also impeding the ability of the mutant urokinase species to fully perform otherwise as does the native single-chain urokinase. In particular it is unnecessary for single-chain urokinase to be converted to two-chain urokinase in vivo in order to activate plasminogen. The mutants provided herein are substantially nonimmunogenic in humans, they remain ultimately fibrin specific and they are capable of activating plasminogen without releasing two-chain urokinase into the vasculature.

BRIEF DESCRIPTION OF THE DRAWINGS

FIG. 1 (designated as FIGS. 1A, 1B, 1C and 1D) depicts the amino acid and nucleotide sequence for human urokinase. The amino acid sequence is shown on the top line, the nucleotide sequence below. Untranslated 5' and 3' regions are also shown.

DETAILED DESCRIPTION

Single-chain urokinase is defined to comprise the protein having the amino acid sequence of human urokinase depicted in FIG. 1 (designated as FIGS. 1A, 1B, 1C and 1D) in its high molecular weight (ca. 54,000 daltons, $NH_2$-$Ser_1$ $Gln_2$ $Glu_3$-terxinus) or its low molecular weight (ca. 33,000 daltons, $NH_2$-$Lys_{136}Pro_{13}$-$7Ser_{138}$-terminus) species, and the amino acid sequence variations and derivatives thereof including natural alleles, wherein the molecule consists of a single amino chain which remains uncleaved at the proteolysis site comprising residues $Arg_{156}$ through $Lys_{158}$ (hereafter the "chain conversion site"). Protease-resistant single-chain urokinase is a urokinase derivative having a single amino acid chain which is less susceptible to proteolytic hydrolysis than the corresponding underivatized, native form of urokinase. In particular, protease resistant urokinase is resistant to conversion to two-chain urokinase by proteolysis at the chain conversion site. Typically, this is determined by incubating the urokinase derivative believed to be protease resistant with human plasmin and comparing the activity of the treated candidate on a chromogenic substrate such as S-2444 in comparison with native single-chain urokinase treated and assayed in the same manner. If the rate of plasmin conversion of the candidate urokinase derivative to the two-chain species (as assayed by an increase in S-2444 hydrolytic activity) is less than about 50%, ordinarily less than 10% of the rate of conversion of the comparable native urokinase to the two-chain species, then the candidate is said to be proteolysis resistant. This procedure is described further in the Examples.

Proteolysis resistant single-chain urokinase also includes single-chain urokinase derivatives which are substantially incapable of proteolytic cleavage at the $Lys_{135}Lys_{136}$ site (hereinafter the "LUK" site). These derivatives are defined as those in which the conversion of HUK to LUK proceeds at a lesser rate with the proteolysis resistant urokinase than with native single-chain urokinase. If the rate of trypsin conversion of the candidate urokinase derivative to the LUK form (as assayed by gel electrophoresis, gel filtration, immunoassay or the like) is less than about 50%, ordinarily less than about 10% of the rate of conversion of the comparable urokinase species to LUK, then the candidate is said to be proteolysis resistant.

Proteolysis resistance also is optionally defined in terms of other proteases to be expected in the environment of the single chain urokinase. Microorganisms employed as hosts for recombinant synthesis of single-chain urokinase contain proteases such as endo and exopeptidases, as well as some esterases or amidases with proteolytic activity. Some of these adventitious proteases will cleave single chain urokinase, and are particularly difficult to deal with during purification when the recombinant urokinase is soluble and may be exposed to elevated concentrations of these proteases. Previously, the answer to this problem has included the use of proteolysis inhibitors, e.g. 1M guanidine HCl, in the purification solvents (3). In addition, an enzyme identified as a single-chain urokinase was isolated from natural sources by rapid separation procedures (6) intended to prevent conversion to the two-chain species.

The protease resistant single-chain urokinase is produced by methods per se known to those skilled in the art. The chain conversion site, and preferably the LUK site as well, are either covalently modified so as to be less susceptible to proteolytic cleavage or are combined with an agent that inhibits access of the protease to the sites.

Agents that inhibit access of the protease include monoclonal antibodies or fragments thereof, e.g. fab fragments, directed against the sites in question or neighboring epitopes positioned so that the bound antibody sterically hinders access of proteases to the site. In this embodiment the urokinase may be a native as well as a mutant molecule, but it is noncovalently associated with another molecule that confers protease resistance. Suitable antibodies or other binding proteins are easily identified by immunizing an animal, e.g. mice against single-chain urokinase in Freund's complete adjuvant, recovering spleen cells from the immunized animal, fusing the cells to produce hybridomas and screening the fusion culture supernatants for antiproteolytic activity. A suitable screening assay is accomplished by first incubating the candidate antibody with single-chain urokinase and then with plasmin, trypsin or any other protease of concern. Thereafter, a protease inhibitor is added to stop the reaction and the fragments separated by gel electrophoresis. A comparison with and without reduction on an electrophoresis gel will demonstrate whether or not the antibody has protected the single-chain urokinase, i.e. the presence of a band migrating with single-chain urokinase on the reducing gel will illustrate the degree of protection afforded the single-chain urokinase.

Another embodiment contemplates the covalent modification of single-chain urokinase at the chain conversion site and, preferably, the LUK site so as to render them less susceptible to proteolytic cleavage. Covalent modification generally is accomplished in one of two ways. In one embodiment, single-chain urokinase is exposed to a derivatizing compound and reacted until at least one residue in a substantial population of the chain conversion or LUK sites is substituted by or sterically hindered by covalent linkage of the urokinase to an organic moiety. The conditions for the reaction are determined by a simple matrix experiment in which preservation of the plasminogen activating activity of the urokinase is compared with increases in proteolytic resistance. Suitable agents are monofunctional compounds which are used under conditions so as to be maximally selective for the side chains of the arginine and, preferably, lysine residues, including 1,2 - cyclohexane dione, acetic anhydride and phenylglyoxal. Undesirable derivatization in the urokinase active site and kringle structure is minimized by conducting the reaction in a stoichiometric excess, respectively, of plasminogen (or other substrate or substrate analogue) and fibrin or benzamidine. Since the agent is monofunctional the proteins will not be crosslinked.

However, the preferred method for producing the protease resistant single-chain urokinase of this invention is to introduce an amino acid sequence variation into the chain conversion or LUK sites by recombinant methods. A DNA sequence that encodes single-chain urokinase is known, as are methods for its expression in recombinant host cells (3,8). Methods are known per se which can be used to introduce mutations into this DNA that are expressed as proteolysis-resistant amino acid sequence variants. For example, DNA segments encoding the chain conversion and LUK sites (as well as flanking regions if necessary) are excised from the urokinase-encoding DNA by sequential digestion with restriction endonucleases, acting at locations flanking the DNA encoding the proteolysis sites (as determined by DNA sequence analysis), recovering the properly cleaved DNA (as determined by gel filtration), synthesizing an oligonucleotide encoding the desired amino acid sequence and flanking regions, digesting with the restriction enzymes also used to excise the undesired fragment, thereby creating cohesive terminii, and ligating the synthetic DNA into the remainder of the single-chain urokinase structural gene. DNA encoding the LUK site, for example, is excised by partial digestion of pUK54trp207-1(3) with MstI and BalI, recovering the vector fragment, and reconstituting the vector by ligating this fragment to a synthetic oligonucleotide having the desired sequence. In this embodiment, DNA encoding [$Lys_{135} \rightarrow \Delta$] human urokinase is created by inserting at the MstI and BalI terminii an oligonucleotide having the sequence

```
pGCAGATGGAAAGCCCTCCTCTCCTCCAGAAGAATTAAAATTTCAGTGTGG
 CGTCTACCTTTCGGGAGGAGAGGAGGTCTTCTTAATTTTAAAGTCACACCp.
•                                                  •
530                                                582
```

(The numbers below the sequence correlate with FIG. 1)

Similarly, the DNA encoding the chain conversion site, for example, is excised by partially digesting the urokinase DNA with BalI and EcoRI in the same fashion and ligating into the opened gene an oligonucleotide bearing the base sequence encoding the desired amino residues. To illustrate, a representative oligonucleotide to be used in preparing [$Arg_{156} \rightarrow His$; $Lys_{158} \rightarrow \Delta$] human urokinase is —HisPheIle—

```
pCCAAAAGACTCTGAGGCCCCACTTTATTATTGGGGGAG
 GGTTTTCTGAGACTCCGGGGTGAAATAATAACCCCCTCTTAAp.
•                                            •
583                                          627
```

Other variant sequences are made by synthesizing and inserting appropriate oligonucleotides in analogous fashion.

However, it is usually more convenient to mutate the urokinase DNA using the M13 phage mutagenesis method (9). This method, which is well known per se.

The amino acid sequence mutants herein are characterized by the deletion or substitution of the basic residues (arginine and/or lysine) found in the protease sites, or the insertion of residues that render the basic residues substantially incapable of participating in proteolytic cleavage. Combinations of insertions, deletions or substitutions are employed. Preferred mutations are set forth in the Table below. This table is not intended to be exclusive of useful mutations.

| Urokinase Residue(s) | Mutational Event |
|---|---|
| 1. $Lys_{135}$ | $\Delta$; or $Lys_{135} \longrightarrow$ His, Ser or Tyr |
| 2. $Lys_{136}$ | $\Delta$; or $Lys_{136} \longrightarrow$ Pro |

-continued

| Urokinase Residue(s) | Mutational Event |
|---|---|
| 3. $Arg_{156}Phe_{157}Lys_{158}$ | $\Delta$; or $Arg_{156}Phe_{157}Lys_{158} \longrightarrow$ $\begin{Bmatrix} His, \\ Ser, \\ Tyr, \\ Glu, \\ or \\ Gly \end{Bmatrix}_{156} Phe_{157} \begin{Bmatrix} His, \\ Ser, \\ Tyr, \\ Glu, \\ or \\ Gly \end{Bmatrix}_{158}$ |
| 4. $Phe_{157}Lys_{158}$ | $\Delta$; or $Phe_{157}Lys_{158} \longrightarrow$ $Phe_{157} \begin{Bmatrix} His, \\ Ser, \\ Tyr, \\ Glu, \\ or \\ Gly \end{Bmatrix}_{158}$ |
| 5. $Lys_{158}$ | $\Delta$; or $Lys_{158} \longrightarrow$ His, Ser, Tyr or Gly |
| 6. $Lys_{158}Ile_{159}$ | $\longrightarrow Lys_{158}ProIle_{159}$ |

If $Lys_{135}$ is undisturbed or mutated to arginine, $Lys_{136}$ should be mutated to proline or deleted. In addition, if $Lys_{158}$ is undisturbed or mutated to arginine, proline should be inserted between $Lys_{158}$ and $Ile_{159}$ or proline substituted for $Ile_{159}$. The most preferred embodiments are the deletion mutants, especially of $Lys_{135}$, $Arg_{156}$ and $Lys_{158}$, closely followed by histidinyl substitutions of these three residues, since such mutations are the least likely to generate autoantibodies in patients. The preferred embodiment is a deletion of $Lys_{135}$ or $Lys_{136}$ combined with a deletion of $Phe_{157}Lys_{158}$. This mutant has the advantage that, even though limited proteolysis does occur after $Arg_{156}$, when proteolytic conversion to the two-chain form does occur the resulting molecule has the same C and N terminii in both urokinase chains as does two chain urokinase (normal proteolysis of prourokinase in vivo releases the Phe Lys dipeptide). Furthermore, with the preferred mutant the molecule remains in the HUK form.

The nucleic acid encoding the protease resistant variant is inserted into an expression vector, the vector used to transform a host cell, the transformant cultured until the variant urokinase accumulates in the culture and the variant then recovered from the culture. The methods for recombinant urokinase preparation described in the published literature (3), which are expressly incorporated by reference, are all satisfactory for preparation of the variants. An exemplary method is described in the Examples below. However, it will be understood that other vectors and host cells are to be used satisfactorily in preparing the variants described herein.

Variant urokinase produced directly in recombinant bacteria (i.e., without the use of a secretory leader) is deposited as intracellular, water-insoluble aggregates called refractile bodies. These are recovered by separating the refractile bodies from cellular debris such as cell wall fragments and the like. This is conveniently accomplished by centrifugation methods, e.g. sucrose gradient separation. Thereafter, the refractile bodies are solubilized in a protein denaturing agent such as 6M guanidine hydrochloride, refolding the protein, the agent removed for example by dialysis and the variant urokinase purified further by classical techniques such as ion exchange resin or gel columns. However, since the variant urokinase is protease resistant it is not necessary to employ benzamidine sepharose to separate single-chain from two-chain urokinase, nor is it necessary to employ either a protease inhibitor (1M guanidine hydrochloride) or rapid separation procedures during the purification steps.

Protease resistant urokinase, whether variant urokinase synthesized in recombinant bacteria, yeast or higher eukaryotic cell cultures, or prepared by covalent or adsorptive modification of native urokinase, is then formulated into a composition for therapeutic administration to patients having blood clots. The urokinase concentration, route of administration and pharmaceutical excipients previously used for native urokinase are equally satisfactory for the protease resistant urokinase of this invention. Typically, about from 10,000 to 75,000 IU/ml of resistant urokinase is formulated into 5% dextrose or other isotonic intravenous vehicle, together with carriers, excipients and stabilizers if desired. The protease-resistant urokinase is infused intravenously at a rate sufficient to achieve perfusion of the occluded artery or vein as ordinarily visualized by conventional techniques, usually greater than about 4,000 IU/Kg/hr. Generally, however, the rate of infusion and the concentration of urokinase will vary considerably based on the activity of the urokinase derivative selected, the general condition of the patient, e.g. the extent of the clot and the hemostatic status of the patient, and the administration route, e.g. by coronary catheter or peripheral administration. The determination of appropriate urokinase concentrations and rates of administration will be within the skill of the ordinary artisan. It should be appreciated that the relative absence of side effects achieved with the present urokinase species facilitates the use of greater doses and rates of administration than has heretofore been possible with two-chain urokinase.

EXAMPLE 1

Construction of Lys$_{136}$→Δ Mutant

Plasmid pUK54trp207*TX was used as the starting plasmid. This plasmid contains DNA encoding the complete HUK gene under the control of the E. coli trp promoter. This plasmid is identical to pUK54trp207-1 (3) except that it contains only one EcoRI site, near the 3' end of the trp promoter, and the 641 bp between the AvaI and PvuII sites of the pBR322 vector component have been deleted (the so-called "XAP" deletion)(14).

Plasmid pUK54trp207-1*TX is made by a known procedure (3) except that the starting plasmid used in that procedure was pHGH207-1*XAP rather than pHGH207-1. pHGH207-1*XAP was produced by partial EcoRI digestion of pHGH207-1 to open the plasmid, the cohesive terminii filled in using the Klenow fragment of DNA polymerase I, the plasmid recircularized using T4 ligase and thereafter used to transform E. coli. A plasmid, pHGH207-1*, was selected in which only the EcoRI site at the 3' end of the trp promoter survived, as determined by restriction enzyme analysis.

In order to effect the XAP deletion, pHGH207-1* was digested with AvaI and PvuII, the large vector fragment recovered, the cohesive terminii filled in using the Klenow fragment of DNA polymerase I, the plasmid blunt-end ligated using the T4 ligase and E. coli transformed with the ligation mixture. pHGH207-1*XAP was recovered and employed in the known method to arrive at pUK54trp207*TX.

pUK54trp207-1*TX was digested with PstI and BclI and the fragment spanning about bases 439 to 732 was recovered. Double stranded M13mp10 (equivalent phage M13mp18 is commercially available from Bethesda Research Laboratories) was digested with PstI and BamHI and annealed to the PstI-BclI urokinase DNA fragment to form M13mp10UK1. E. coli JM101 cells (ATCC No. 33876) were transformed with the double stranded replicative form (RF) of M13mp10UK1. The single stranded and RF M13mp10UK1 were isolated from infected E. coli JM101 cells in known fashion. Note that BclI and BamHI form cohesive terminii, so that the M13mp10 phage was able to recircularize with the urokinase insert. The single stranded form was used for the site specific mutagenesis of urokinase at the Lys$_{136}$ site.

A synthetic oligonucleotide was prepared by the solid phase phosphotriester method (16) for use as a mutagenesis primer. The following primer was used for the deletion of Lys$_{136}$:

This is the portion of the urokinase coding strand flanking Lys$_{136}$ except that the AAG codon for Lys$_{136}$ was deleted.

The procedure described hereinafter was used to generate a urokinase clone containing the mutated sequence of the synthetic primers. This procedure is generally known per se (9).

50 ng of the synthetic oligonucleotide was phosphorylated for 30 minutes at 37° C. in 10 μl of a mixture and 50 mM Tris-HCl pH 7.5, 10 mM MgCl$_2$, 10 mM dithiothreitol, 1 mM ATP containing 8 U of T4 polynucleotide kinase. For use as a probe, 400 ng of the synthetic oligonucleotide was phosphorylated as above except that ATP was replaced with 60 mCi [γ$^{32}$P]-ATP (3000 Ci/mmol) resulting in approximately 50 to 60×10$^6$ cpm/400 ng of 24mer. For heteroduplex formation, 100 ng single stranded M13mp10UK1 was heated to 95° C. (10 min), and slowly cooled to room temperature over a 30 min time period in 40μl of a mixture containing 10 mM Tris-HCl pH 7.5, 10 mM MgCl$_2$, 1 mM dithiothreitol, and 10 ng of the phosphorylated primer and 500 ng of EcoRI-digested M13mp10UK1 large fragment. Primer extension was started by the addition of 10 μl buffer containing 50 mM Tris HCl pH.7.5, 10 mM MgCl$_2$ and 1 mM dithiothreitol, 2 mM ATP, 0.25 mM each of dGTP, dTTP, dCTP and dATP, 5 U of E. coli DNA polymerase I large fragment and 400 U of T4 DNA ligase. After 1 hr at 12° C. the reaction mixture was used to transform E. coli JM101 cells.

Transformation was accomplished by mixing 10 μl of the ligation mixture with 200 μl of competent JM101 cells, followed by incubation for 30 min on ice and 5 min at 37° C. Then 3.5 ml 2YT top agar at 55° C. was mixed with 300 μl saturated JM101 cells, 10 μl IPTG (200 mM) and 50 μl Xgal and after addition of the transformed cells plated on 9 cm Petri dishes containing LB with no drugs.

Two colorless plaques (B2 and G12) were picked and transferred to a microtiter dish containing 100 μl YT medium. The inoculated microtiter fluids were stamped on 15 cm diameter LB agar plates overlayed with a lawn of 600 μl JM101 cells in 8 ml 2YT top agar and incubated overnight at 37° C. The formed plaques were transferred to a nitrocellulose disc by physical contact for 1 min. The nitrocellulose disc was treated with 0.5 M NaOH, 1.5 M NaCl for 3 min and washed twice with 3 M NaCl-0.5 M TrisHCl pH 7.5 for 15 min and then with 2X SSC for 15 min. Prehybridization mix contains 10 mM Tris pH 7.5, 5 mM EDTA, 0.9 M NaCl, 1X Denhardt, 0.5 percent NP40, 100 μM ATP, 1 mM sodium pyrophosphate, 1 mM sodium phosphate and 50 μg/ml E. coli tRNA. 1X Denhardt's contains per liter 200 mg Ficoll, 200 mg polyvinylpyrrolidone, 200 mg bovine serum albumin (BSA; fraction V). The disc was baked at 80° C. in vacuo for 90 min. the disc was then incubated for 3 hrs with 6 ml prehybridization fluid in a Petri dish followed by addition of $5 \times 10^6$ cpm labeled primer and hybridized overnight. Selective washing of the disc was performed with 0.4X SSC at 49° C. and after air-drying the disc was exposed to X-ray film. The positively hybridizing clones were further analyzed by dideoxy sequencing. The B2 clone was confirmed to contain the proper sequence containing the $Lys_{136}$ deletion.

The expression plasmid was reconstituted by ligating XbaI-BclI and XbaI-PstI fragments from pUK54trp207-1*TX with the Sau3A-PstI insertion fragment from plaque B2 and transforming the ligation mixture into E. coli. A transformant was selected which contained a plasmid carrying the mutant gene (pUK54B2). The fragments were obtained by conventional restriction enzyme digestion and recovery of the fragment desired. While in doing so the BclI and BamHI sites are both destroyed, note that the M13 urokinase insert was excised at the same point as the BclI and BamHI ligation by Sau3A, which recognizes the center four bases of any of the BclI, BamHI or BclI-BamHI ligation sites.

pUK54B2 was used to transform E. coli. At the present time the preferred strain of E. coli is W3110fhuA−. This strain is not essential for the preparation of the urokinase mutants herein, but it is more convenient because it is more resistant to contaminating phage and thus more practical for commercial scale synthesis.

E. coli W3110 fhuA− is a T1 phage resistant bacterium characterized by a deletion or inversion of DNA sequences associated with the fhuA gene as disclosed in co-pending U.S. patent application Ser. No. 06/673,955 filed Nov. 21, 1984, now abandoned. Briefly, E. coli W3110 (ATCC 27325) is transduced with lambda bacteriophage containing the transposable element Tn10 which confers tetracycline resistance. Strains of Tn10 transduced W3110 are selected for resistance to phage infection. Phage resistant strains are pooled and infected with bacteriophage P1. The resulting lysate is used to transduce E. coli AT982 (17). Strain AT982 contains a DAP mutation located close to the fhuA gene. Accordingly, transduction of strain AT982 by the P1 lysate and selection of transductants which are tetracycline resistant and which regenerate the DAP function indicates that transposon Tn10 is located within the fhuA gene. Strains which are tetracycline resistant and demonstrate regenerated DAP function are the source of DNA for bacteria phage P1 transduction of E. coli W3110. Transduced W3110 strains expressing tetracycline resistance and phage resistance are selected. These strains are then selected on the basis of resistance to phage infection and reversion to tetracycline sensitivity (18). The reversion to tetracycline sensitivity coupled with the retention of resistance to T1 phage infection indicates that DNA sequence associated with the fhuA gene have either been deleted or inverted irreversibly. Strains so constructed are designated E. coli W3110 fhuA−.

The phage containing the transposable element Tn10 which was used to insert Tn10 into W3110 was constructed as follows. The starting material was lambda c1857b 2210am29. This phage is known to those skilled in the art (19), and was constructed from three well known mutants of lambda phage by standard procedures. A lysate of this lambda phage was prepared on the amber suppressor E. coli C600 (ATCC No. 23724) which had been manipulated by procedures known to those skilled in the art to also carry the Tn10 transposon (19). This lysate was used to infect E. coli C600 (lambda C1857) which contains an amber suppressor and a lambda prophage carrying the c1857 genotype. Lysates of tetracycline resistant colonies were prepared by heat induction by growing the tetracycline resistant colonies first in broth at 32° C. and thereafter at 42° C. for 90 minutes. The lysate was then plated on E. coli C600 and replica plated. The plaques appearing on E. coli C600 were replica plated at 32° C. on E. coli C600 and E. coli W3102 sup+ (lambda imm434) which contains the heteroimmune prophage lambda imm434 (20). Plaques appearing on the heteroimmune strain are plated onto tetracycline plates. Plaques appearing on these plates are capable of transducing tetracycline resistance and are used in the above described method for generating E. coli W3110 fhuA−.

Recombinant native and [$Lys_{136} \rightarrow \Delta$] human urokinase were obtained from 1 liter cultures of W3110 or W3110FhuA− cells transformed with the appropriate plasmid. Expression was induced further by addition of indoleacrylic acid.

EXAMPLE 2

Construction of [$Lys_{136} \rightarrow 66$; $Phe_{157}Lys_{158} \rightarrow \Delta$] Human Urokinase Substantially the same procedure was followed in generating expression plasmids carrying other or additional mutants. It is convenient in some instances to use the M13 phage already carrying one or more mutants in the preparation of DNA mutated at additional sites. The following procedure was used to prepare [$Phe_{157}Lys_{158} \rightarrow \Delta$; $Lys_{136}-\Delta$] human urokinase. M13mp10UK1 was used as a template for a primer having the following sequence:

5′ pCTGAGGCCCCGCATTATTGGGGGA.
    •                         •
   593                621

Using the method above, plaque 2F3 was identified. Phage from plaque 2F3 were determined to carry a urokinase DNA fragment containing the $Phe_{157}Lys_{158} \rightarrow \Delta$ mutation. The expression plasmid for this mutation which also contains the Lys$_{136}$ deletion mutation (Ex. 1) was reconstituted by ligating the vector fragment from a BalI-BclI digestion of pUK54B2 with the BalI-Sau3A insertion fragment of phage 2F3, transforming and culturing E. coli W3110 or W3110FhuA$^-$. Transformed cells were grown on minimal media overnight, to an O. D. at 550 nm of 1.2. Additional media was added. Indole acrylic acid, a compound which further induces expression of the tryptophan operon controlled genes, was added to a concentration of 10 μg/ml. The cells were incubated 2 hours and harvested.

While pUK54trp207-1*TX was the plasmid actually used in the preparation of the protease-resistant urokinase sequence variants described herein, it will be appreciated by those skilled in the art that other expression vectors are suitable for use herein. All that is needed is cloned DNA encoding urokinase. This DNA is obtained by synthesis or by obtaining mRNA from suitable cells, e.g. Detroit 562 cells (ATCC No. CCL 138), and preparing cDNA therefrom (3). This DNA is identified by at least substantial DNA and amino acid sequence homology with the native urokinase sequence shown in FIG. 1. Suitable restriction enzyme sites are identified from the DNA sequence and employed, together with adaptors or linkers as required, to obtain DNA suitable for insertion into the selected expression vector. The use of other plasmid constructions and host-vector systems will be within the skill of the art.

EXAMPLE 3

Purification of [Lys$_{136}$→Δ; Phe$_{157}$Lys$_{158}$→Δ] Human Urokinase 200 gm of cell paste, harvested from half of the 10 liter fermenter fermentation conducted as described in Example 2, was homogenized at 4° C. in 10 liters of 0.05M Tris, pH 7.2, containing 0.02M EDTA, 0.5 gm/liter lysozyme (Sigma) and 0.01 gm/liter each of ribonuclease (Sigma) and deoxyribonuclease (Sigma). The solution was passed three times through a Menton Gaulin mill at 4,500 psi and centrifuged for 30 minutes at 4,700× g at 5° C. The resulting pellet, which contains urokinase as monitored by SDS-PAGE and Western blotting, was resuspended by homogenization in 500 ml of 0.05M Tris and 0.02M EDTA, pH7.2. This suspension was layered over 1.3 liters of 50% glycerol and centrifuged again for 30 minutes at 4,700×g.

The urokinase which again is found in the pellet, was dissolved with stirring for 6 to 8 hours, in 300 ml 6.0M guanidine hydrochloride at 4° C. Insoluble material was removed by centrifugation for 30 minutes at 4,700×g. The supernatant was diluted to 6.0 liters for refolding. The final concentration of salts in the pH 9.0 refolding buffer was: 0.05M Tris, 1.0M guanidine hydrochloride, 0.2M arginine, 0.005M EDTA, 0.005% Tween 80, 1.25 mM reduced glutathione and 0.25 mM oxidized glutathione. The volume of 6.0 liters was calculated to give an OD$_{280}$ ≦1. The solution was allowed to stand 24 hours at 4° C. to obtain maximal yields of activity as measured by fibrin plate assay. Refolding reagents were removed by dialysis at 4° C. against two changes of 60 liters each of 0.05M sodium phosphate, pH 6.8 containing 0.005% Tween 80. The dialysis was completed overnight. All subsequent purification steps were carried out at 4° C.

The dialyzed solution was batch extracted with 400 mls of DE-52 cellulose (Whatman) equilibrated in the dialysis buffer. The slurry was filtered using a Buchner funnel. The supernatant, containing unadsorbed urokinase, was loaded immediately onto a 100 ml (5×5 cm) hydroxylapatite (BioRad) column previously equilibrated with the dialysis buffer. The column was washed with 0.125M sodium phosphate, pH 6.8 containing 0.005% Tween 80. Urokinase was eluted with 0.4M sodium phosphate, pH 6.8 containing 0.005% Tween 80.

The elution pool from the hydroxylapatite column was concentrated to approximately 30 ml using a YM10 Amicon filter and was loaded onto a 2.5×130 cm Sephacryl S-200 sizing column equilibrated with 0.05M sodium phosphate, pH 6.8 containing 1.0M guanidine hydrochloride and 0.005% Tween 80. The peak containing urokinase was pooled and dialyzed against 100 volumes of 0.05M sodium phosphate, pH 7.3, containing 0.15M sodium chloride and 0.005% Tween 80.

EXAMPLE 4

Activity of [Lys$_{136}$→Δ; Phe$_{157}$Lys$_{158}$→Δ] Human Urokinase

Urokinase and its mutants were assayed on fibrin plates (11). The fibrin plates consisted of 1.25% agarose, 4.1 mg/ml human fibrinogen, 0.3 units/ml of thrombin and 0.5 μg/ml of soybean trypsin inhibitor. Urokinase and its mutants also were assayed as noted by direct chromogenic substrate, S-2444 (Helena Laboratories, Beaumont, Texas) (12). All assays were compared to the urokinase standard (Calbiochem) for absolute activities.

The relative activities of [Lys$_{136}$→Δ;Phe$_{157}$Lys$_{158}$→Δ] human recombinant urokinase, recombinant native HUK (3) and native HUK were compared by fibrin plate assay. The results were 96,250, 126,200 and 121,200 Ploug Units (PU)/mg, respectively. This demonstrates that the three amino acid deletions did not substantially modify the plasminogen activating capacity of the mutant urokinase. 300 PU of the mutant contained only 0.76 PU by S-2444 chromogenic activity. This was only about 0.25% of the S-2444 activity of native urokinase. It was concluded that the mutant exhibited either some residual S-2444 activity or that limited conversion to the two-chain form had occured.

A comparison of the activity of plasmin on [Lys$_{136}$→Δ;Phe$_{157}$ Lys$_{158}$→Δ] human urokinase and recombinant single chain native urokinase was conducted. When 0.0625 units of plasmin were added to 300 PU (fibrin plate) of mutant and incubated for 1 hour at 37° C., enzyme was produced having an S-2444 activity of 10.36 PU, whereas a much smaller quantity of plasmin (0.005 units) incubated for a shorter period (15 min) at 37° C. with 50 PU of recombinant single-chain native urokinase yielded enzyme having a much greater S-2444 activity(∼45 PU). The comparative S-2444 specific activities of two chain and plasmin incubated recombinant native and recombinant mutant urokinases are shown below.

| Enzyme | S-2444 Activity (PU × 10$^3$/mg) |
| --- | --- |
| recombinant single-chain HUK | 89.0 |
| 2 chain recombinant HUK | 102.2 |
| 2 chain native HUK | 92.7 |
| mutant recombinant single-chain HUK | 3.3 |

Thus, the mutant is far less susceptible to plasmin activation than is the native molecule.

BIBLIOGRAPHY

1. Gunzler, W. A., et al. The primary structure of high molecular mass urokinase from human urine: The complete amino acid sequence of the A chain. "Hoppe Seyler's Z. Physiol. Chem. Bd." 363: 1155–1165 (1982).
2. Steffens, G. J., et al. The complete amino acid sequence of low molecular mass urokinase from human urine. "Hoppe-Seyler's Z. Physiol. Chem. Bd." 363: 1043–1058 (1982).
3. EP Publication No. 92182.
4. Wun, T-C, et al A Proenzyme Form of Human Urokinase. "Journal of Biological Chemistry" 257: 7262–7268 (1982).
5. Nielsen, L. S., et al. Purification of Zymogen to Plasminogen Activator from Human Glioblastoma cells by Affinity Chromatography with Monoclonal Antibody. "Biochemistry" 21: 6410–6415 (1982).
6. U.S. Pat. No. 4,381,346.
7. Zamarron et al., Competitive Inhibition by Human Plasma of the Activation of Plasminogen by Pro-Urokinase in "Thrombosis and Haemostasis" 54(1): abs.604, pp 102, (Jul. 14, 1985).
8. Heyneker, H. et al., Functional Expression of the human urokinase gene in *Escherichia coli* in "Genetics of Industrial Microorganisms, 1982, Proceedings of the IVth International Symposium" K. Ikeda et al. Eds., pp 214–221 (1983).
9. Adelman, J. et al., In Vitro Deletional Mutagenesis for Bacteial Production of the 20,000-Dalton Form of Human Pituitary Growth Hormone. "DNA" 2(3): 183–193 (1983).
10. Winter, G. et al., Redesigning Enzyme Structure by Site-directed Mutagenesis: Tyrosyl tRNA Synthetase and ATP Binding. "Nature" 290: 756–758 (1982).
11. Ploug, J. et al., Urokinase: An activator of plasminogen from human urine. I. Isolation and Porperties. "Biochim. Biophys. Acta" 24: 278–282 (1957).
12. Hayashi, S. et al., Assay of urokinase activity in plasma with a chromogenic substrate. "Thrombosis Research" 22: 573–578 (1981).
13. Gray et al. "Bio/Technology" 2: 161–165 (February 1984).
14. Sutcliff, Cold Spring Harbor Symposium on Quantitative Biology, 43: 77 (1979).
15. Goeddel, D., et al.. "Nature" 287: 411 (1980).
16. Crea et al., "Proc. Nat. Acad. Sci. USA" 75: 5765 (1978).
17. Bukhari, et al., "J. Bacteriology" 105:844 (1971).
18. Naloy et al., "J. Bacteriology" 145: 1110 (1981).
19. Kleckner et al., "J. Mol. Biol." 116: 125 (1977).
20. Kleckner et al., "Genetics" 90: 427 (1978).

We claim:

1. An isolated protease resistant human urokinase polypeptide having a mutant amino acid sequence at residues $Arg_{156}$ $Phe_{157}$ $Lys_{156}$.

2. The polypeptide of claim 1 wherein the urokinase is ($Phe_{157}$ $Lys_{158}\rightarrow\Delta$) urokinase.

3. The polypeptide of claim 1 wherein the urokinase further includes a mutant amino acid sequence residues $Lys_{135}$ $Lys_{136}$.

4. The polypeptide of claim 1 wherein the urokinase is converted upon incubation with human plasmin to two-chain urokinase at a rate of less than about 10% of the rate of conversion of native single-chain urokinase.

5. The polypeptide of claim 1 wherein the urokinase is less susceptible to proteolytic conversion to two-chain urokinase than is native single-chain urokinase.

6. The polypeptide of claim 1 wherein the urokinase is selected from the group of ($Phe_{157}Lys_{158}\rightarrow\Delta$) human urokinase, ($Phe_{157}Lys_{158}$ $Lys_{136}\rightarrow\Delta$) human urokinase, ($Arg_{158}$) human urokinase, ($His_{158}$) human urokinase, ($Gly_{158}$) human urokinase, ($Ser_{158}$) human urokinase, ($Tyr_{158}$) human urokinase, ($Arg_{156}\rightarrow His$; $Lys_{158}\rightarrow Ser$) human urokinase, ($Arg_{156}Lys_{158}\rightarrow\Delta$) human urokinase, ($Arg_{156}$ $Phe_{157}$ $Lys_{158}\rightarrow\Delta$) human urokinase, ($Lys_{158}$ $Ile_{159}\rightarrow Lys_{158}$ Pro $Ile_{159}$) human urokinase, ($Phe_{157}$ $Lys_{158}\rightarrow\Delta$; $Arg_{156}\rightarrow His$) human urokinase, and ($Arg_{156}$ $Phe_{157}\rightarrow\Delta$; $Lys_{158}\rightarrow Gly$) human urokinase.

7. The polypeptide of any one of claims 1, 2, 3, 4, 5, or 6 in therapeutically effective concentration in a pharmacologically acceptable excipient.

8. A modified human urokinase having a mutated amino acid sequence at residues Art-156 Phe-157 Lys-158 Iso-159.

9. A modified human urokinase according to claim 8 further including a mutated amino acid sequence at residues Lys-135 Lys-136.

10. A protease resistant, modified human urokinase having a mutated amino acid sequence at (a) residues Arg-156 Phe-157 Lys-158, (b) residues Lys-135 Lys-136, or (c) residues Arg-156 Phe-157 Lys-158 and residues Lys-135 Lys-136.

11. A protease resistant, modified human urokinase have a mutated amino acid sequence at residues Lys-135 Lys-136.

* * * * *

UNITED STATES PATENT AND TRADEMARK OFFICE
CERTIFICATE OF CORRECTION

PATENT NO. : 5,219,569
DATED : 15 June 1993
INVENTOR(S) : Blaber, et al.

It is certified that error appears in the above-identified patent and that said Letters Patent is hereby corrected as shown below:

In column 2, line 17, replace "fora" with --form--.

In column 3, line 7, replace "terxinus" with --terminus--.

In column 6, line 55, underline "in vivo".

In column 9, line 10, insert --2-- before "YT".

In column 9, line 26, capitalize "t" in "the".

In column 11, line 34, replace "fermenter" with --fermentor--.

Signed and Sealed this

Fifteenth Day of March, 1994

Attest:

BRUCE LEHMAN

*Attesting Officer*   *Commissioner of Patents and Trademarks*